US012780771B2

(12) United States Patent
Aquino et al.

(10) Patent No.: US 12,780,771 B2
(45) Date of Patent: Nov. 3, 2026

(54) ORGANIC TERTIARY OR QUATERNARY AMMONIUM SALTS AS CATALYSTS IN THE FORMATION OF GAMMA, DELTA-UNSATURATED KETONES

(71) Applicant: DSM IP ASSETS B.V., Heerlen (NL)

(72) Inventors: Fabrice Aquino, Kaiseraugst (CH); Werner Bonrath, Kaiseraugst (CH); Francesco Pace, Kaiseraugst (CH)

(73) Assignee: DSM IP ASSETS B.V., Maastricht (NL)

( * ) Notice: Subject to any disclaimer, the term of this patent is extended or adjusted under 35 U.S.C. 154(b) by 568 days.

(21) Appl. No.: 18/264,160

(22) PCT Filed: Feb. 7, 2022

(86) PCT No.: PCT/EP2022/052850
§ 371 (c)(1),
(2) Date: Aug. 3, 2023

(87) PCT Pub. No.: WO2022/167643
PCT Pub. Date: Aug. 11, 2022

(65) Prior Publication Data

US 2024/0308948 A1 Sep. 19, 2024

(30) Foreign Application Priority Data

Feb. 8, 2021 (EP) .................................... 21155687

(51) Int. Cl.
*C07C 45/51* (2006.01)
*B01J 31/02* (2006.01)

(52) U.S. Cl.
CPC ......... *C07C 45/513* (2013.01); *B01J 31/0285* (2013.01)

(58) Field of Classification Search
CPC ........................... C07C 45/513; B01J 31/0285
See application file for complete search history.

(56) References Cited

U.S. PATENT DOCUMENTS 8,664,450 B2 * 3/2014 Aquino ................ C07C 45/511
568/403

FOREIGN PATENT DOCUMENTS

| | | |
|---|---|---|
| CN | 106478514 | 3/2017 |
| WO | WO 2017/097884 | 6/2017 |

OTHER PUBLICATIONS

Written Opinion of the ISA for PCT/EP2022/052850 mailed May 3, 2022, 5 pages.
Notice of Reasons for Rejection, JP Application No. 2023-544253, May 13, 2025 (EN Translation).

* cited by examiner

*Primary Examiner* — Sikarl A Witherspoon
(74) *Attorney, Agent, or Firm* — NIXON & VANDERHYE P.C.

(57) ABSTRACT

The present invention relates to the manufacture of gamma, delta-unsaturated ketones from tertiary vinyl carbinols and vinylic ethers or ketals using an organic tertiary or quaternary ammonium salt as catalyst.

26 Claims, 1 Drawing Sheet

ORGANIC TERTIARY OR QUATERNARY AMMONIUM SALTS AS CATALYSTS IN THE FORMATION OF GAMMA, DELTA-UNSATURATED KETONES

CROSS-REFERENCE TO RELATED APPLICATIONS

This application is the U.S. national phase of International Application No. PCT/EP2022/052850 filed Feb. 7, 2022 which designated the U.S. and claims priority to EP patent application Ser. No. 21/155,687.3 filed Feb. 8, 2021, the entire contents of each of which are hereby incorporated by reference.

TECHNICAL FIELD

The present invention relates to the manufacturing of gamma, delta-unsaturated ketones.

BACKGROUND OF THE INVENTION

Gamma, delta-unsaturated ketones of the formula (I) are an important class of industrial chemicals and are central products in the synthesis of vitamins and aroma ingredients. particularly important. One of the possible synthetic routes uses tertiary vinyl carbinols as starting products.

G. Saucy et al. disclose in Helv. Chim. Acta 1967, 50, 2091-2095 and Helv. Chim. Acta 1967, 50, 2095-2100 that phosphoric acid or sulfuric acid or p-toluene sulfonic acid can be used as catalyst for the reaction between tertiary vinyl carbinols and isopropenyl ethers.

C. Wang et al. disclose in Green Chemistry 2009, 11, 6, 843-847 a Saucy-Marbet reaction of tertiary propargyl alcohols and unsaturated ethers in the presence of ammonium ionic liquids. This reaction leads to allene ketones which are not gamma-, delta-unsaturated ketones.

However, the use of strong acid in is disadvantageous as these chemicals are hazardous in the handling and use special protection methods and require specific and corrosion-resistant materials for the equipment used in the manufacturing process DE 196 49 564 discloses that diverse organophosphorous compounds as catalysts.

WO 2010/046199 A2 discloses inorganic ammonium ($NH_4^+$) salts as potential catalysts. However, inorganic ammonium salts have typically a disadvantageous solubility and it been shown that the inorganic ammonium salts show lower yields and selectivities particularly when used at concentrations of less than 1 mol-%.

SUMMARY OF THE INVENTION

Figure 1:
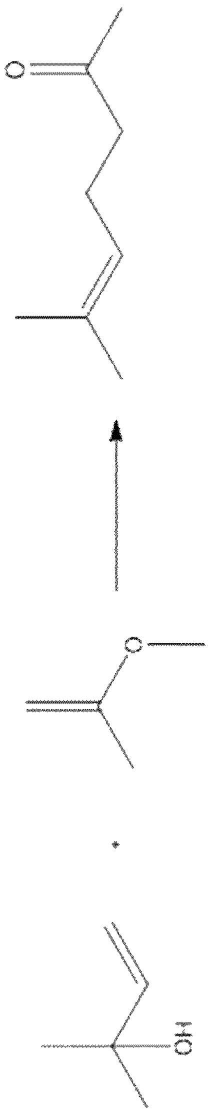
FIG. 1 is a reaction scheme to obtain 6-methyl-5-hepten-2-one by the reaction of 2-methyl-3-buten-2-ol ("MBE") with isopropenyl methyl ether ("IPM") according to Experimental series 1 below.

Therefore, the problem to be solved by the present invention is to offer a process with a high yield and selectivity using a catalyst having a suitable solubility under the absence of strong acids and corrosive conditions.

Surprisingly, it has been found that a process according to the claim 1 and the reaction mixture according to claim 17 are able to solve this problem. It has been found that organic tertiary and quaternary ammonium salts are particularly well suited as catalyst for said reaction. It has been found that particularly well suited organic tertiary and quaternary ammonium salts catalysts the ones which have anions which comprise a phosphor atom been bound to at least one oxygen atom.

Further aspects of the invention are subject of further independent claims. Particularly preferred embodiments are subject of dependent claims.

Detailed Description of the Invention

In a first aspect the present invention relates to a process for the manufacture of gamma, delta-unsaturated ketones of the formula (I)

(I)

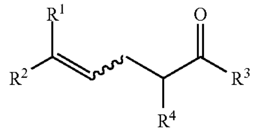

by reaction of a compound of the formula (II) with a compound of the formula (IIIa) or (IIIb)

(II)

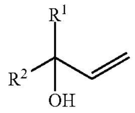

(IIIa)

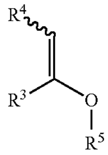

(IIIb)

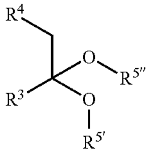

in the presence of an organic tertiary or quaternary ammonium salt as catalyst;

wherein $R^1$ represents a methyl or ethyl group;

$R^2$ represents a saturated or unsaturated linear or branched or cyclic hydrocarbyl group with 1 to 46 C atoms;

$R^3$ represents a methyl or an ethyl group;

$R^4$ represents H or methyl or an ethyl group;

$R^5$ represents a linear or branched $C_{1-10}$-alkyl group, particularly a methyl or an ethyl group;

$R^{5'}$ and $R^{5''}$ represent either a linear or branched $C_{1-10}$-alkyl group, particularly a methyl or an ethyl group;

or $R^{5'}$ and $R^{5''}$ form together a linear or branched $C_{1-10}$-alkylene group, particularly an ethylene or propylene group;

and wherein the wavy line represents a carbon-carbon bond and which when linked to the carbon-carbon double bond is either in the Z or in the E-configuration.

For sake of clarity, some terms used in the present document are defined as follows:

In the present document, a "$C_{x-y}$-alkyl" group is an alkyl group comprising x to y carbon atoms, i.e., for example, a $C_{1-3}$-alkyl group is an alkyl group comprising 1 to 3 carbon atoms. The alkyl group can be linear or branched. For example —$CH(CH_3)$-$CH_2$-$CH_3$ is considered as a $C_4$-alkyl group.

In case identical labels for symbols or groups are present in several formulae, in the present document, the definition of said group or symbol made in the context of one specific formula applies also to other formulae which comprises the same said label.

The term "independently from each other" in this document means, in the context of substituents, moieties, or groups, that identically designated substituents, moieties, or groups can occur simultaneously with a different meaning in the same molecule.

The term "organic" in the term "organic tertiary or quaternary ammonium salt" in this document relates to the ammonium cation. Therefore, "organic tertiary or quaternary ammonium salt" in the present document means any salt which comprises an organic tertiary or quaternary ammonium entity. In contrast to this any ammonium salt which comprises $NH_4^+$ is regarded as inorganic ammonium salt. Hence, e.g. tetrabutylammonium chloride or triethylammonium bromide or tetrabutylammonium acetate are regarded as organic tertiary or quaternary ammonium salts, whereas e.g. ammonium sulphate ($(NH_4)_2SO_4$) or ammonium acetate ($CH_3COONH_4$) are not regarded as organic tertiary or quaternary ammonium salts.

In the present document, any dotted line in formulae represents the bond by which a substituent is bound to the rest of a molecule.

In the present document, any wavy line represents independently from each other a carbon-carbon bond which when linked to the carbon-carbon double bond is either in the Z or in the E-configuration.

Compound of the formula (II) is reacted either with a compound of the formula (IIIa) or of the formula (IIIb) in the presence of a catalyst (="Cat") being an organic tertiary or quaternary ammonium salt.

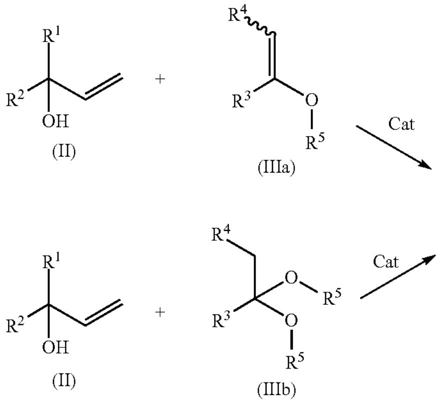

(II) (IIIa)
(II) (IIIb)

-continued

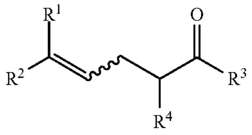
(I)

Compound of the Formula (II)

The compounds of the formula (II) are substances known to the person skilled in the art.

$R^1$ represents a methyl or ethyl group, preferably a methyl group.

$R^2$ represents a saturated or unsaturated linear or branched or cyclic hydrocarbyl group with 1 to 46 C atoms, preferably a methyl group.

In a preferred embodiment, $R^2$ represents a group which is selected from the group consisting of the formula (R2-I), (R2-II), (R2-III) and (R2-IV)

(R2-I)
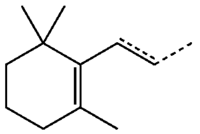
(R2-II)
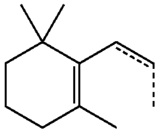
(R2-III)
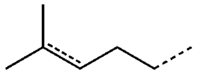
(R2-IV)
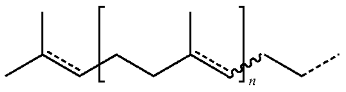

The dotted line represents the bond by which the substituent of the formula (R2-1), (R2-II), (R2-III) or (R2-IV) is bound to the rest of the compound of the formula (I) or formula (II). Any double bond having dotted line ------ represents independently from each other either a single carbon-carbon bond or a double carbon-carbon bond. Any wavy line represents independently from each other a carbon-carbon bond which when linked to the carbon-carbon double bond is either in the Z or in the E-configuration.

In the above formulae n represents 1, 2, 3 or 4, particularly 1 or 2.

In one of the preferred embodiments, $R^2$ represents either a group of the formula (R2-I) or of the formula (R2-II).

In another preferred embodiment, $R^2$ represents either a group of the formula (R2-III) or of the formula (R2-IV).

It is particular preferred that the compound of the formula (II) is selected from the group consisting of 2-methyl-3-buten-2-ol ("MBE"), 3-methyl-4-penten-3-ol ("EBE"), 3,7-dimethyl-1,6-octadien-3-ol (=linalool, "LL"), 3,7-dimethyl-1-octen-3-ol ("DMOE") and 3,7,11-trimethyl-1,6-dodecadien-3-ol (nerolidol, "NL"), particularly (6E)-3,7,11-trimethyl-1,6-dodecadien-3-ol (=E-nerolidol, "E-NL").

It is even more preferred that the compound of the formula (II) is 2-methyl-3-buten-2-ol ("MBE") or 3,7-dimethyl-1,6-octadien-3-ol (=linalool, "LL").

Compound of the Formula (IIIa)

The compounds of the formula (IIIa) are substances known to the person skilled in the art.

In formula (IIIa) $R^3$ represents a methyl or an ethyl group and $R^4$ represents H or methyl or an ethyl group and $R^5$ represents $R^5$ represents a linear or branched $C_{1-10}$-alkyl group, particularly a methyl or an ethyl group.

Preferably, the group $R^3$ represents a methyl group.

Preferably, the group $R^4$ represents H.

Preferably, the group $R^5$ represents a methyl group.

The compound of the formula (IIIa) is most preferably either isopropenyl methyl ether ("IPM") or isopropenyl ethyl ether ("IPE"), particularly isopropenyl methyl ether ("IPM").

Due to the synthesis of compound of the formula (IIIa), very often also mixtures of compounds of the formula (IIIa) are used for the reaction with compound of the formula (II). For example, for butenyl methyl ether, often a mixture of 2-methoxybut-1-ene and (E)-2-methoxybut-2-ene and (Z)-2-methoxybut-2-ene being prepared from methanol and methyl ethyl ketone, is used.

Compound of the Formula (IIIb)

The compounds of the formula (IIIb) are substances known to the person skilled in the art.

In formula (IIIb) $R^3$ represents a methyl or an ethyl group and $R^4$ represents H or methyl or an ethyl group.

$R^{5'}$ and $R^{5''}$ represent in one embodiment each either a linear or branched $C_{1-10}$-alkyl group, particularly a methyl or an ethyl group. In another embodiment, $R^{5'}$ and $R^{5''}$ form together a linear or branched $C_{1-10}$-alkylene group, particularly an ethylene or propylene group.

Preferably, the group $R^3$ represents a methyl group.

Preferably, the group $R^4$ represents H.

In one preferred embodiment, $R^{5'}{=}R^{5''}$ and particularly $R^{5'}{=}R^{5'}$=methyl or ethyl, more preferably $R^{5'}{=}R^{5'}{=}CH_3$.

In another preferred embodiment, $R^{5'}$ and $R^{5''}$ form together an ethylene ($CH_2CH_2$) or propylene ($CH_2CH_2CH_2$ or $CH(CH_3)CH_2$) group.

The compound of the formula (IIIb) is most preferably either 2,2-dimethoxypropane or 2,2-diethoxypropane or 2,2-dimethyl-1,3-dioxolane or 2,2,4-tri-methyl-1,3-dioxolane or 2,2-dimethyl-1,3-dioxane.

The compound of the formula (IIIb) is most preferably either 2,2-dimethoxypropane or 2,2-diethoxypropane, particularly 2,2-dimethoxypropane.

The use of the compound of formula (IIIa) is preferred over the compound of the formula (IIIb).

Organic Tertiary or Quaternary Ammonium Salt as Catalyst

The reaction of a compound of the formula (II) with a compound of the formula (IIIa) or (IIIb) is performed in the presence of an organic tertiary or quaternary ammonium salt as catalyst.

In one of the preferred embodiments, the catalyst is an organic tertiary ammonium salt and has a cation of the formula (IV)

(IV)

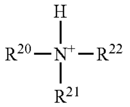

wherein $R^{20}$, $R^{21}$ and $R^{22}$ represent independently from each other a linear or branched $C_{1-18}$-alkyl or cycloalkyl group.

It is preferred that $R^{20}$, $R^{21}$ and/or $R^{22}$ represent linear $C_{1-18}$-alkyl groups.

It is more preferred that $R^{20}$, $R^{21}$ and/or $R^{22}$ represent either a methyl or an ethyl group.

It is further preferred that $R^{20}{=}R^{21}{=}R^{22}$.

It is particularly preferred that $R^{20}{=}R^{21}{=}R^{22}$=methyl or ethyl.

In one of the other preferred embodiments, the catalyst is an organic tertiary ammonium salt and has a cation of the formula (V)

(V)

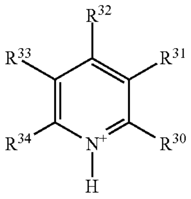

wherein $R^{30}$, $R^{31}$, $R^{32}$, $R^{33}$ and $R^{34}$ represent independently from each other either H or a linear or branched $C_{1-12}$-alkyl or $C_{5-12}$-cycloalkyl group.

It is preferred that $R^{30}{=}R^{31}{=}R^{32}{=}R^{33}$, preferably $R^{30}{=}R^{31}{=}R^{32}{=}R^{33}{=}H$.

It is further preferred that one of the groups of $R^{30}$, $R^{31}$, $R^{32}$, $R^{33}$ and $R^{34}$ is a methyl group.

It is also preferred that $R^{34}$ represents a methyl group or H, preferably H.

Most preferred as tertiary ammonium compound of the formula (V) is pyridinium or α-picolinium or β-picolinium or γ-picolinium, preferably pyridinium.

In one of the other preferred embodiments, the catalyst is an organic quaternary ammonium salt and has a cation of the formula (VI)

(VI)

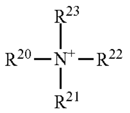

wherein $R^{20}$, $R^{21}$, $R^{22}$ and $R^{23}$ represent independently from each other a linear or branched $C_{1-18}$-alkyl or cycloalkyl group.

It is preferred that $R^{20}$ $R^{21}$, $R^{22}$ and/or $R^{23}$ represent linear $C_{1-18}$-alkyl groups.

It is more preferred that $R^{20}$, $R^{21}$ and/or $R^{22}$ represent either a methyl or an ethyl group.

It is further preferred that $R^{20}{=}R^{21}{=}R^{22}{=}R^{23}$.

It is particularly preferred that $R^{20}{=}R^{21}{=}R^{22}{=}R^{23}$=ethyl or butyl, preferably butyl.

The organic tertiary or quaternary ammonium salts can be easily formed from their respective tertiary amine by protonation respectively by alkylation.

It has been found that the catalysts organic tertiary or quaternary ammonium salts show particularly high yields and selectivities in the desired product of the formula (I) when the anion of the organic tertiary or quaternary ammonium salt comprises a phosphor atom which is bound to at least one oxygen atom, preferably selected from the group consisting of $PO_4^{3-}$, $HPO_4^{2-}$, $H_2PO^{4-}$, $P_2O_7^{3-}$, $HP_2O_7^{2-}$ and $H_3P_2O^{7-}$.

It has been found that the reaction is preferably performed when the molar ratio of the compound of the formula (II) to the compound of the formula (IIIa) or (IIIb) is ranging from 1:15 to 1:1.

In case of using the compound of the formula (IIIa), said ratio is more preferred in the range from 1:5 to 1:2, more preferably ranging from 1:3.5 to 1:2, most preferably ranging from 1:3 to 1:2, particularly ranging from 1:2.5 to 1:2.

In case of use of the compound of the formula (IIIb) said ratio is more preferred in the range from 1:10 to 1:2, more preferably ranging from 1:8 to 1:3, most preferably ranging from 1:8 to 1:5.

Furthermore, it is preferred that the amount of the organic tertiary or quaternary ammonium salt is ranging from 0.01-0.3 mol-%, preferably ranging from 0.02-0.1 mol-%, more preferably ranging from 0.02-0.07 mol-%, based on the amount of the compound of the formula (II).

It has been, surprisingly, found that even when organic tertiary or quaternary ammonium salt catalysts are used below 1 mol-%, particularly below 0.7 mol-%, the ratio of the compound of the formula (II) to the compound of the formula (IIIa) or (IIIb) still can be used between 1:3 to 1:2, particularly 1:2.5 to 1:2 which significant lowering of selectivity and/or yield in the compound of the formula (I).

The reaction is preferably carried out at a temperature ranging from 100 to 170° C., more preferably at a temperature ranging from 110 to 160° C., most preferably at a temperature ranging from 120 to 150° C.

The reaction is preferably carried out at a pressure ranging from 5 to 15 bar, more preferably at a pressure ranging from 8 to 12 bar.

The reaction can be carried out without solvent or in the presence of an organic solvent. Preferably the reaction is carried out without solvent.

Even if the reaction is carried out in the absence of an organic solvent, the starting materials, the compounds of the formula (II) and (IIIa) or (IIIb), as well as said an organic tertiary or quaternary ammonium salt may still be provided in an organic solvent. Thus, there may be an amount of organic solvent up to 10 weight-%, preferably an amount of organic solvent up to 5 weight-%, more preferably an amount of organic solvent up to 3 weight-%, based on the total weight of the reaction mixture.

If the reaction is carried out in an organic solvent, polar aprotic organic solvents such as aliphatic ketones as e.g. acetone are preferred.

It has been found that the above reaction provides the compound of the formula (I) in high conversion, yield and selectivity.

It has been found that particularly the compound of the formula (I) being selected from the group consisting of 6-methyl-5-hepten-2-one, 6-methyl-5-octen-2-one, 6,10-dimethyl-5,9-undecadien-2-one, 6,10-dimethyl-5-undecen-2-one, 6,10,14-trimethylpentadeca-5,9-dien-2-one, 6,10,14-trimethylpentadeca-5,13-dien-2-one and 6,10,14-trimethyl-5,9,13-pentadeca-trien-2-one, preferably 6-methyl-5-hepten-2-one or 6,10-dimethyl-5,9-undecadien-2-one can be preferably produced.

The reaction mixture itself, with or without an organic solvent, is also an object of the present invention.

Thus, the present invention relates in a further aspect to a reaction mixture comprising a compound of the formula (II), (II)

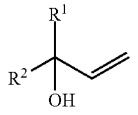

a compound of the formula (IIIa) or (IIIb)

(IIIa)

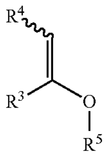

(IIIb)

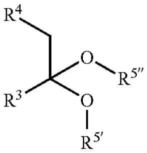

and a catalyst being an organic tertiary or quaternary ammonium salt.

The compound of the formula (II) and of the formula (IIIa) or (IIIb) as well as the catalyst being an organic tertiary or quaternary ammonium salt have been discussed to a great extend already above.

EXAMPLES

The present invention is further illustrated by the following non-limiting experiments.

Experimental Series 1

2-methyl-3-buten-2-ol ("MBE") was mixed with 2.1 equivalents of isopropenyl methyl ether ("IPM") in the presence of the respective catalyst, and stirred at a temperature of 150° C. during reaction time as given in table 1. The respective product, i.e. 6-methyl-5-hepten-2-one, was obtained in the yield and selectivity as indicated in table 1 (see FIG. 1).

TABLE 1

Formation of 6-methyl-5-hepten-2-one from 2-methyl-3-buten-2-ol and isopropenyl methyl ether (2.1 equivalent) using ammonium salts at 150° C. and a pressure of 8.5 bara

| Example | Ammonium salt[1] | Type[2] | Amount[3] [mol %] | Reaction time [h] | Yield [%] | Selectivity [%] |
|---|---|---|---|---|---|---|
| 1 | $(Et_3NH)H_2PO_4$ | tert. | 0.18 | 24 | 92 | 93 |
| 2 | $(Et_3NH)_2HPO_4$ | tert. | 0.15 | 24 | 91 | 94 |
| 3 | $(pyH)H_2PO_4$ | quat. | 0.10 | 16 | 91 | 92 |
| 4 | $(pyH)H_3P_2O_7$ | quat. | 0.1 | 16 | 89 | 89 |
| 5 | $(Et_3NH)HSO_4$ | tert. | 0.01 | 16 | 43 | 43 |
| 6 | $(Bu_4N)HSO_4$ | quat. | 0.1 | 16 | 41 | 43 |

[1]$(Et_3NH)$ = triethylammonium; (pyH) = pyridinium; $(Bu_4N)$ = tetrabutylammonium
[2]tert. = tertiary ammonium salt; quat. = quaternary ammonium salt
[3]amount of catalyst relative to 2-methyl-3-buten-2-ol

Experimental Series 2

Figure 2:
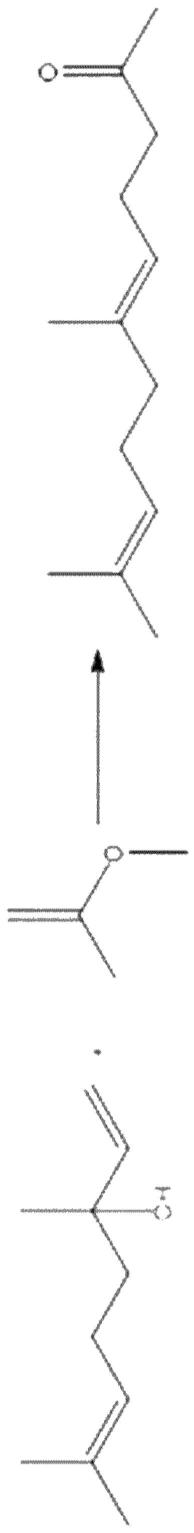
FIG. 2 is a reaction scheme to obtain 6,10-dimethylundeca-5,9-dien-2-one by the reaction of 3,7-dimethylocta-1,6-dien-3-ol ("LL") with isopropenyl methyl ether ("IPM") according to Experimental series 2 below.

3,7-dimethylocta-1,6-dien-3-ol ("LL") was mixed with the number of equivalents given in table 2 of isopropenyl methyl ether ("IPM") in the presence of respective catalyst in the amount as given in table 2, and stirred at a temperature of 150° during 16 hours. The respective product, i.e. 6,10-dimethyl undeca-5,9-dien-2-one, was obtained in the yield and selectivity as indicated in table 2 (see FIG. 2).

TABLE 2

Formation of 6,10-dimethyl-5,9-undecadien-2-one from 3,7-dimethyl-1,6-octadien-3-ol and isopropenyl methyl ether (IPM) using ammonium salt at 150° C. and a pressure of 8.5 bara during a reaction time of 16 hours.

| Example | Ammonium salt[1] | Type[2] | Amount IPM[3] [eq] | Amount[4] [mol %] | Yield [%] | Selectivity [%] |
|---|---|---|---|---|---|---|
| 7 | $(pyH)H_3P_2O_7$ | quat. | 2.1 | 0.2 | 72.8 | 73 |
| 8 | $(pyH)H_3P_2O_7$ | quat. | 2.5 | 0.2 | 82.7 | 83 |
| 9 | $(pyH)H_2PO_4$ | quat. | 2.1 | 0.2 | 81.1 | 84 |
| 10 | $(pyH)H_2PO_4$ | quat. | 2.5 | 0.2 | 86.0 | 87 |
| 11 | $(Et_3NH)H_2PO_4$ | tert. | 2.1 | 0.2 | 74.37 | 91.4 |
| 12 | $(Et_3NH)H_2PO_4$ | tert. | 2.5 | 0.2 | 77.24 | 93.2 |
| 13 | $(Et_3NH)_2HPO_4$ | tert. | 2.1 | 0.2 | 71.61 | 93.7 |
| 14 | $(Et_3NH)_2HPO_4$ | tert. | 2.5 | 0.2 | 76.05 | 94.3 |
| Ref. 1 | $(NH_4)HSO_4$ | inorg. | 2.1 | 0.2 | 11.3 | 11 |
| Ref. 2 | $(NH_4)HSO_4$ | inorg. | 2.5 | 0.2 | 14.2 | 14 |
| Ref. 3 | $(NH_4)_2HPO_4$ | inorg. | 2.1 | 0.2 | 48.5 | 96 |
| Ref. 4 | $(NH_4)_2HPO_4$ | inorg. | 2.5 | 0.2 | 32.2 | 97 |

[1](pyH) = pyridinium; $(Et_3NH)$ = triethylammonium
[2]tert. = tertiary ammonium salt; quat. = quaternary ammonium salt; inorg. = inorganic ammonium salt
[3]amount of IPM relative to 3,7-dimethyl-1,6-octadien-3-ol
[4]amount of catalyst relative to 3,7-dimethyl-1,6-octadien-3-ol

The invention claimed is:

1. A process for manufacturing gamma, delta-unsaturated ketones of the formula (I):

(I)

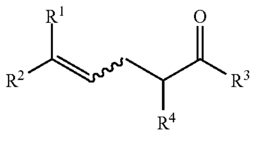

wherein the process comprises reacting a compound of the formula (II) with a compound of the formula (IIIa) or (IIIb):

(II)

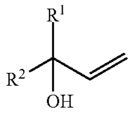

-continued (IIIa)

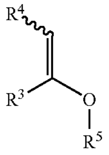

(IIIb)

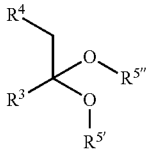

in the presence a catalyst comprised of an organic tertiary ammonium salt having a cation according to formulas (IV) or (V), or an organic quaternary ammonium salt having a cation according to formula (VI):

(IV)

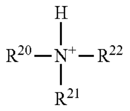

(V)

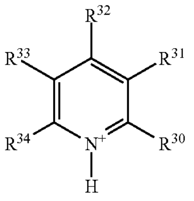

(VI)

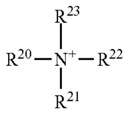

wherein;

$R^1$ represents a methyl or ethyl group;

$R^2$ represents a saturated or unsaturated linear or branched or cyclic hydrocarbyl group with 1 to 46 C atoms;

$R^3$ represents a methyl or an ethyl group;

$R^4$ represents H or methyl or an ethyl group;

$R^5$ represents a linear or branched $C_{1-10}$-alkyl group, particularly a methyl or an ethyl group;

$R^{5'}$ and $R^{5''}$ either (i) represent a linear or branched $C_{1-10}$-alkyl group, particularly a methyl or an ethyl group, or (ii) form together a linear or branched $C_{1-10}$-alkylene group;

$R^{20}=R^{21}=R^{22}=R^{23}$ and represent a linear or branched $C_{1-18}$-alkyl or cycloalkyl group, and $R^{30}$, $R^{31}$, $R^{32}$, $R^{33}$ and $R^{34}$ represent independently from each other either H or a linear or branched $C_{1-12}$-alkyl or $C_{5-12}$-cycloalkyl group, and wherein the wavy line represents a carbon-carbon bond and which when linked to the carbon-carbon double bond is either in the Z or in the E-configuration.

2. The process according to claim 1, wherein $R^{20}=R^{21}=R^{22}=R^{23}$=methyl or ethyl.

3. The process according to claim 1, wherein $R^{30}=R^{31}=R^{32}=R^{33}$.

4. The process according to claim 1, wherein $R^{34}$ represents a methyl group or H.

5. The process according to claim 1, wherein characterized in $R^{20}=R^{21}=R^{22}=R^{23}$=ethyl or butyl.

6. The process according to claim 1, wherein the anion of the organic tertiary or quaternary ammonium salt comprises a phosphor atom which is bound to at least one oxygen atom.

7. The process according to claim 1, wherein $R^1$ represents a methyl group.

8. The process according to claim 1, wherein a molar ratio of the compound of the formula (II) to the compound of the formula (IIIa) or formula (IIIb) is from 1:15 to 1:1.

9. The process according to claim 1, wherein the organic tertiary or quaternary ammonium salt is present in an amount from 0.01-0.3 mol-%, based on the amount of the compound of the formula (II).

10. The process according to claim 1, wherein $R^2$ is selected from the group consisting of the formula (R2-I), (R2-II), (R2-III) and (R2-IV), (R2-I)

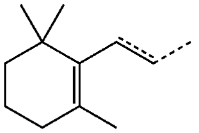

(R2-II)

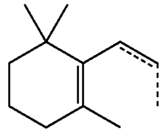

(R2-III)

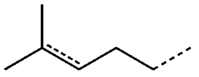

(R2-IV)

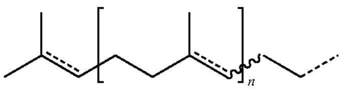

wherein the dotted line represents the bond by which the substituent of the formula (R2-I), (R2-II), (R2-III) or (R2-IV) is bound to the rest of the compound of the formula (I) or formula (II);

and wherein any double bond having dotted line (═══) represents independently from each other either a single carbon-carbon bond or a double carbon-carbon bond;

and wherein any wavy line represents independently from each other a carbon- carbon bond which when linked to the carbon-carbon double bond is either in the Z or in the E-configuration;

and wherein n represents 1, 2, 3 or 4, particularly 1 or 2.

11. The process claim 1, wherein the compound of the general formula (I) is selected from the group consisting of 6-methyl-5-hepten-2-one, 6-methyl-5-octen-2-one, 6,10-dimethyl-5,9-undecadien-2-one, 6,10-dimethyl-5-undecen-2-one, 6,10, 14-trimethylpentadeca-5,9-dien-2-one, 6,10,14-trimethylpentadeca-5, 13-dien-2-one and 6,10,14-trimethyl-5,9,13-pentadeca-trien-2-one.

12. The process according to claim 1, wherein $R^{5'}$ and $R^{5''}$ form together an ethylene or propylene group.

13. The process according to claim 1, wherein $R^{30}=R^{31}=R^{32}=R^{33}$=H.

14. The process according to claim 6, wherein the anion of the organic tertiary or quaternary ammonium salt is selected from the group consisting of $PO_4^{3-}$, $HPO_4^{2-}$, $H_2PO_4$, $P_2O_7^{3-}$, $HP_2O_7^{2-}$ and $H_3P_2O_{7\_}$.

15. The process according to claim 1, wherein the molar ratio of the compound of the formula (II) to the compound of the formula (IIIa) is from 1:5 to 1:2.

16. The process according to claim 1, wherein the molar ratio of the compound of the formula (II) to the compound of the formula (IIIa) is from 1:3.5 to 1:2.

17. The process according to claim 1, wherein the molar ratio of the compound of the formula (II) to the compound of the formula (IIIa) is from 1:3 to 1:2.

18. The process according to claim 1, wherein the molar ratio of the compound of the formula (II) to the compound of the formula (IIIa) is from 1:2.5 to 1:2.

19. The process according to claim 1, wherein the molar ratio of the compound of the formula (II) to the compound of the formula (IIIb) is from 1:10 to 1:2.

20. The process according to claim 1, wherein the molar ratio of the compound of the formula (II) to the compound of the formula (IIIb) is from 1:8 to 1:3.

21. The process according to claim 1, wherein the molar ratio of the compound of the formula (II) to the compound of the formula (IIIb) is from 1:8 to 1:5.

22. The process according to claim 1, wherein the organic tertiary or quaternary ammonium salt is present in an amount from 0.02-0.1 mol-%,-based on the amount of the compound of the formula (II).

23. The process according to claim 1, wherein the organic tertiary or quaternary ammonium salt is present in an amount from 0.02-0.07 mol-%, based on the amount of the compound of the formula (II).

24. A reaction mixture comprising:

a compound of the formula (II):

(II)

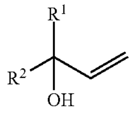

a compound of the formula (IIIa) or (IIIb):

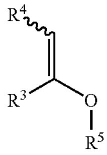

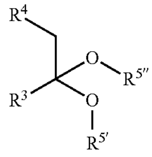

and a catalyst, wherein the catalyst comprises an organic tertiary or quaternary ammonium salt having a cation according to formulas (IV) or (V), or an organic quaternary ammonium salt having a cation according to formula (VI):

(IV)

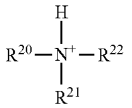

(V)

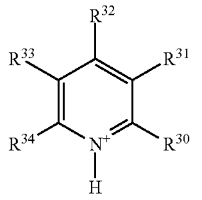

(VI)

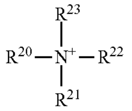

wherein $R^1$ represents a methyl or ethyl group;

$R^2$ represents a saturated or unsaturated linear or branched or cyclic hydrocarbyl group with 1 to 46 C atoms;

$R^3$ represents a methyl or an ethyl group;

$R^4$ represents H or methyl or an ethyl group;

$R^5$ represents a linear or branched $C_{1-10}$-alkyl group, particularly a methyl or an ethyl group;

$R^{5'}$ and $R^{5''}$ either (i) represent a linear or branched $C_{1-10}$-alkyl group; or (ii) form together a linear or branched $C_{1-10}$-alkylene group;

$R^{20}$=$R^{21}$=$R^{22}$=$R^{23}$ and represent a linear or branched $C_{1-18}$-alkyl or cycloalkyl group, and $R^{30}$, $R^{31}$, $R^{32}$, $R^{33}$ and $R^{34}$ represent independently from each other either H or a linear or branched $C_{1-12}$-alkyl or $C_{5-12}$-cycloalkyl group, and wherein the wavy line represents a carbon-carbon bond and which when linked to the carbon-carbon double bond is either in the Z or in the E-configuration.

25. The reaction mixture according to claim 24, wherein $R^{5'}$ and $R^{5''}$ form together an ethylene or propylene group.

26. The process according to claim 6, wherein the anion of the organic tertiary or quaternary ammonium salt is selected from the group consisting of $PO_4^{3-}$, $HPO_4^{2-}$, $H_2PO_4$, $P_2O_7^{3-}$, $HP_2O_7^{2-}$, and $H_3P_2O_7$.

* * * * *